(12) United States Patent
Golijanin et al.

(10) Patent No.: US 8,725,225 B2
(45) Date of Patent: May 13, 2014

(54) INTRAOPERATIVE IMAGING OF RENAL CORTICAL TUMORS AND CYSTS

(75) Inventors: Dragan Golijanin, Rochester, NY (US); Edward M. Messing, Rochester, NY (US)

(73) Assignee: University of Rochester, Rochester, NY (US)

( * ) Notice: Subject to any disclaimer, the term of this patent is extended or adjusted under 35 U.S.C. 154(b) by 1031 days.

(21) Appl. No.: 11/836,737

(22) Filed: Aug. 9, 2007

(65) Prior Publication Data

US 2008/0161662 A1     Jul. 3, 2008

Related U.S. Application Data

(60) Provisional application No. 60/837,414, filed on Aug. 10, 2006.

(51) Int. Cl.
    *A61B 5/00*     (2006.01)

(52) U.S. Cl.
    USPC ............ 600/317; 600/407; 600/417; 600/476

(58) Field of Classification Search
    USPC .................................. 600/317, 407, 417, 476
    See application file for complete search history.

(56) References Cited

U.S. PATENT DOCUMENTS

| | | | |
|---|---|---|---|
| 6,351,663 B1 | 2/2002 | Flower et al. | |
| 7,229,774 B2* | 6/2007 | Chinnaiyan et al. | 435/7.1 |
| 2003/0130575 A1* | 7/2003 | Desai | 600/417 |
| 2008/0154102 A1* | 6/2008 | Frangioni et al. | 600/317 |

OTHER PUBLICATIONS

Riefke et al., "In vivo characterization of cyanine dyes as contrast agents for near-infrared imaging", Proc. SPIE 2927, Optical Imaging Techniques for Biomonitoring, II, 199-207, Dec. 11, 1996.*
De Grand, A.M. and J.V. Frangioni, "An operational near-infrared fluorescence imaging system prototype for large animal surgery," 2003, *Technology in Cancer Research & Treatment*, vol. 2(6), pp. 1-10.
Demos, S.G., et al., "Near-infrared autofluorescence imaging for detection of cancer," 2004, *J. Biomed. Opt.*, vol. 9(3), pp. 587-592.
Frangioni, John V., "In vivo near-infrared fluorescence imaging," 2003, *Current Opinion in Chemical Biology*, vol. 7, pp. 626-634.
Haglund, M.M., et al., "Enhanced optical imaging of rat gliomas and tumor margins," 1994, *Neurosurgery*, vol. 35(5), pp. 930-941.
Herts, Brian R., "Imaging for renal tumors," 2003, *Curr. Opin. Urol.*, vol. 13, pp. 181-186.
Humblet, V., et al., "High-affinity near-infrared fluorescent small-molecule contrast agents for in vivo imaging of prostate-specific membrane antigen," 2005, *Mol. Imaging*, vol. 4(4), pp. 448-462.
Jamis-Dow, C.A., et al., "Small (≤3-cm) renal masses: Detection with CT versus US and pathologic correlation," 1996, *Radiology*, vol. 198, pp. 785-788.
Marangos, N., et al., "In vivo visualization of the cochlear nerve and nuclei with fluorescent axonal tracers," 2001, *Hearing Research*, vol. 162, pp. 48-52.
Nakayama, A., et al., "Functional near-infrared fluorescence imaging for cardiac surgery and targeted gene therapy," 2002, *Mol. Imaging*, vol. 1(4), pp. 365-377.

* cited by examiner

*Primary Examiner* — Baisakhi Roy

(57) ABSTRACT

The invention provides methods for visualizing renal tumors and for staging cysts during an operation by use of a fluorescent dye.

27 Claims, No Drawings

INTRAOPERATIVE IMAGING OF RENAL CORTICAL TUMORS AND CYSTS

CROSS-REFERENCES TO RELATED APPLICATIONS

This application claims the benefit of U.S. Provisional Application No. 60/837,414, filed Aug. 10, 2006, the contents of which are hereby incorporated by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

A variety of medical techniques have been used for imaging biological tissues and organs are known. These include traditional x-rays, ultra-sound, magnetic resonance imaging (MRI), and computerized tomography (CT). Techniques such as MRI, micro-CT, micro-positron emission tomography (PET), and single photon emission computed tomography (SPECT) have been explored for imaging function and processes in small animals or in vivo, intra operatively. These technologies offer deep tissue penetration and high spatial resolution, but are costly and time consuming to implement.

A variety of dyes useful for medical imaging have been described, including radio opaque dyes, fluorescent dyes, and calorimetric dyes (see e.g., U.S. Pat. Nos. 5,699,798; 5,279, 298; 6,351,663). Imaging techniques and systems using fluorescent dyes have been described for some organs, such as the eye (see, e.g., U.S. Pat. No. 5,279,298) In the eye, some dyes can serve both an imaging function and a therapeutic function (see, e.g., U.S. Pat. No. 6,840,933). Non-toxic tracers such as Indocyanine Green (ICG), fast blue, and fluorogold, have been used in mammals without evidence of neuronal toxicity several months after the treatment (Thielert et al., J Comp Neurol. 337(1):113 (1993); Yeterian et al., Exp Brain Res. 99(3):383 (1994); vogt Weisenhorn et al., J Comp Neurol. 362(2):233 (1995)).

In one study for use of ICG in surgical procedures, nine patients undergoing surgery for the removal of intrinsic brain tumors with enhanced optical imaging was performed using ICG as an intravenous contrast-enhancement agent. Optical images were obtained before and after injection of the ICG. The patients in the study showed differences in the dynamic optical signals among normal brain, low-grade astrocytomas, and malignant astrocytomas. Optical imaging of the resection margins in malignant tumors showed differences between adjacent normal tissue and remaining tumor tissue. Haglund, M. et al., Enhanced optical imaging of human gliomas and tumor margins. Neurosurgery, 38(2):308-317 (1996).

Renal cortical malignancies are the seventh most commonly diagnosed cancer in the US. Approximately 36,160 new cases of renal cancers were diagnosed in 2005, (22,490 in men and 13,670 in women), and about 12,660 people (8020 men and 4640 women) died from this disease. These statistics include both adults and children with renal cell carcinomas, Wilms' tumors and transitional cell carcinomas of the renal pelvis. Eliminating upper urinary tract transitional cell carcinoma and childhood tumors from the number of all renal neoplasms, renal cortical tumors accounted for more than 31,500 new cases in 2005. Most people with renal cell cancer are at middle age with its peak incidence between the ages of 50 and 74. Mortality, accounting for 3% of all cancer related deaths, has remained unchanged despite the increase in disease incidence. For reasons that are not completely clear, the kidney cancer rate has been increasing about 1.5% per year. This is likely due to incidental cancer detection during diagnostic procedures such as ultrasound and abdominal CT scans. With the increasing detection of incidental renal lesions, the evaluation and management of solid and cystic renal tumors are of even greater importance to physicians dealing with renal cell cancer.

Improved quality and readily available imaging has substantially increased the number of incidental renal tumors detected. Multiple studies showed that disease-free survival rates were similar between cancers treated with radical and partial nephrectomy. The surgical management of renal cell carcinoma has undergone significant changes over the past fifteen years. Initially treated with radical nephrectomy, most cases of renal cell carcinoma are now approached with nephron-sparing surgical technique irrespective of tumor size.

More recent issues regarding partial nephrectomy have been complication rates and their subsequent management, renal cell carcinoma multifocality, margin status, distance to normal renal parenchyma, cost analysis, and the development of minimally invasive techniques with similar success and complication rate as open partial nephrectomy. (Desai, M. et al., Laparoscopic partial nephrectomy versus laparoscopic cryoablation for the small renal tumor. Urology, 66(5 Suppl): 23-28 (2005), Diblasio, C. et al., Mini-flank supra-11th rib incision for open partial or radical nephrectomy, BJU Int, 97(1):149-156 (2006), Gill, I. et al., Comparative analysis of laparoscopic versus open partial nephrectomy for renal tumors in 200 patients. J Urol, 170(1):64-68 (2003)). Newer and more technologically advanced techniques developed during the last 10 years to treat small cortical lesions include radiofrequency ablation (RFA), cryoablation, and high intensity focused ultrasound (HIFU). Currently, all of these procedures are being performed either percutaneously, laparoscopically or as a part of open procedure. (Weizer, A. et al., Complications after percutaneous radiofrequency ablation of renal tumors, Urology, 66(6):1176-1180 (2005), Ahrar, K. et al., Percutaneous radiofrequency ablation of renal tumors: technique, complications, and outcomes. J Vasc Interv Radiol, 16(5):679-688 (2005)).

Not all tumors amenable to partial nephrectomy are easily seen at surgery. Significant subsets of the tumors are located intracortically, intrarenally or in the renal hilar area. To better assess these tumors, intra operative ultrasound with or without needle localization has been developed to increase the negative margin rate while decreasing resection of normal renal tissue or necessitate the conversion to open radical nephrectomy. To date, there are no reported studies that have reviewed cancer control in patients undergoing renal sparing surgery with intra operative ultrasound. Similarly, multifocality of renal cortical tumors is well known and poses a difficult task for the urologic surgeon.

Multifocal tumor occurrence is a clear risk factor for cancer recurrence, progression of disease and the need for additional surgeries. Intra operative ultrasound is the only imaging modality used in assessment of small satellite lesions. Pre operatively, lesions that are 8-10 mm in size can be characterized using CT and MRI. Many times there will be small (<8 mm) lesions present that can not be visualized with current day CT and MRI scanners and are only noticed intra operatively. Unfortunately, in some cases unexpected intra operative findings of multifocal tumor lesions will preclude partial nephrectomy and necessitate conversion to radical nephrectomy. All these increase the risk of chronic renal insufficiency and possibly the need for dialysis. (McKieman, J. et al., Natural history of chronic renal insufficiency after partial and radical nephrectomy. Urology, 59(6): p. 816-820 (2002)). Nephron-sparing surgery provides effective therapy for patients with borderline renal insufficiency or in whom preservation of renal function is a critical clinical consideration.

Meticulous operative technique is of utmost importance for achieving acceptable oncologic and functional outcomes. To further improve partial nephrectomy results, intra operative imaging has been introduced, mainly using intra operative ultrasound. This method requires an experienced ultrasonographer and special equipment, and sometimes results in time consuming imaging without successful demonstration of clear margins. (Assimos, D. et al., Intraoperative renal ultrasonography: a useful adjunct to partial nephrectomy. J Urol, 146(5): p. 1218-1220 (1991)).

Despite its drawbacks, intra operative ultrasonography has proven valuable in delineating tumor extent and margins during nephron-sparing surgery and in evaluating the presence of synchronous multifocality. Several investigators have found intra operative ultrasound to be helpful in characterizing renal lesions. Findings on intra operative ultrasound have changed the intra operative approach in 17 to 33% of select patients planned for partial nephrectomy. The reported mean cancer specific survival of all patients undergoing nephron-sparing surgery for any indication is 72%-100%. In more recent studies, selection criteria were better defined and the disease specific survival rate exceeded 90%.

It would be desirable to have a less cumbersome technique that can be performed by all members of the surgical team and which can increase the opportunity to spare nephrons without compromising the ability to remove tumors. The present invention fills these and other needs.

BRIEF SUMMARY OF THE INVENTION

The present invention provides methods for detecting the presence or absence of a tumor in an area of a kidney in a subject during a surgical operation, comprising: a) administering to the subject a dye which fluoresces at an emission wavelength when the dye is contacted with an excitation wavelength, wherein the dye is administered to the subject either systemically or locally into vasculature providing blood directly into the kidney; b) exposing the kidney during the operation to a source of illumination comprising the excitation wavelength under conditions such that fluorescent dye in the kidney fluoresces; and, c) detecting the presence or absence of fluorescence of the dye in the kidney during the operation, wherein detecting absence of fluorescence in the area indicates the presence of a tumor in the area, and detecting the presence of fluorescence in the area indicates the absence of a tumor in the area. In some embodiments, there are a plurality of tumors in said kidney. In some embodiments, the dye is administered intravenously. In some embodiments, the dye is administered locally into the renal artery, the superior segmental artery, anterior superior segmental artery, anterior inferior segmental artery, inferior segmental artery, an arcuate artery, or an interlobular artery. In some embodiments, the tumor is visualized on a image display. In some embodiments, the exposing of the kidney to the illumination comprising the excitation wavelength is by a laproscopic instrument. In some embodiments, the dye is a near infrared dye. In some embodiments, the dye is a tricarbocyanine dye or an analog thereof. In some embodiments, the tricarbocyanine dye is indocyanine green. In some embodiments, the subject is a human. In some embodiments, the dye is administered during the surgical operation. In some embodiments, the dye is administered within 1 hour before the surgical operation. In some embodiments, the dye is administered within about ½ hour before said surgical operation.

In a further group of embodiments, the invention provides methods for visualizing a tumor in a kidney in a subject during a surgical operation, comprising: a) administering to the subject a dye which fluoresces at an emission wavelength when the dye is contacted with an excitation wavelength, wherein the dye is administered to the subject either systemically or locally into vasculature providing blood directly into the kidney; b) exposing the kidney during the operation to a source of illumination comprising the excitation wavelength under conditions such that fluorescent dye in the kidney fluoresces; and, c) visualizing the presence or absence of fluorescence of the dye in the kidney during the operation, wherein visualizing an area of the kidney in which fluorescence is absent is a visualization of the tumor. In some embodiments, there are a plurality of tumors in the kidney. In some embodiments, the dye is administered intravenously. In some embodiments, the dye is administered locally into the renal artery, the superior segmental artery, anterior superior segmental artery, anterior inferior segmental artery, inferior segmental artery, an arcuate artery, or an interlobular artery. In some embodiments, the tumor is visualized on a image display. In some embodiments, the exposing of the kidney to the illumination comprising the excitation wavelength is by a laproscopic instrument. In some embodiments, the dye is a near infrared dye. In some embodiments, the dye is a tricarbocyanine dye or an analog thereof. In some embodiments, the tricarbocyanine dye is indocyanine green. In some embodiments, the subject is a human. In some embodiments, the dye is administered during said surgical operation. In some embodiments, the dye is administered within 1 hour before said surgical operation. In some embodiments, the dye is administered within about ½ hour before said surgical operation.

In yet a further group of embodiments, the invention provides methods for visualizing a tumor margin in tissue excised from a kidney during a surgical operation, comprising: a) administering to the subject a dye which fluoresces at an emission wavelength when the dye is contacted with an excitation wavelength, b) excising some or all of a tumor and surrounding tissue from the kidney during the operation, c) exposing the some or all of the tumor and surrounding tissue to a source of illumination comprising the excitation wavelength such that any fluorescent dye in some or all of the tumor fluoresces; and, d) visualizing the presence or absence of fluorescence of the dye, wherein visualizing fluorescence around the some or all of said tumor indicates the presence of a tumor margin, and an absence of fluorescence around some or all of the tumor indicates the absence of a tumor margin. In some embodiments, there are a plurality of tumors in said kidney. In some embodiments, the dye is administered intravenously. In some embodiments, the dye is administered locally into the renal artery, the superior segmental artery, anterior superior segmental artery, anterior inferior segmental artery, inferior segmental artery, an arcuate artery, or an interlobular artery. In some embodiments, the excised tumor and any surrounding tissue is visualized on a image display. In some embodiments, the dye is a near infrared dye. In some embodiments, the dye is a tricarbocyanine dye or an analog thereof. In some embodiments, the tricarbocyanine dye is indocyanine green. In some embodiments, the subject is a human.

In yet a further group of embodiments, the invention provides methods of determining during a surgical operation whether a cyst in a kidney in a subject is benign or contains malignant cells, comprising: a) administering to said subject a dye which fluoresces at an emission wavelength when said dye is contacted with an excitation wavelength, wherein said dye is administered to said subject either systemically or locally into vasculature providing blood directly into said kidney; b) exposing said cyst during said operation to a source of illumination comprising said excitation wavelength under conditions such that fluorescent dye in said cyst fluoresces; and, c) comparing the fluorescence of said dye in said cyst during said operation to the fluorescence of surrounding kidney tissue, wherein bright fluorescence in said cyst compared to said surrounding kidney tissue indicates that the cyst is benign and low or no fluorescence in said cyst compared to said surrounding kidney tissue indicates that the cyst contains malignant cells. In some embodiments, the dye is administered intravenously. In some embodiments, the dye is administered locally into the renal artery, the superior segmental artery, anterior superior segmental artery, anterior inferior segmental artery, inferior segmental artery, an arcuate artery, or an interlobular artery. In some embodiments, the cyst is visualized on a image display. In some embodiments, the exposing of said cyst to said illumination comprising said excitation wavelength is by a laproscopic instrument. In some embodiments, the dye is a near infrared dye. In some embodiments, the dye is a tricarbocyanine dye or an analog thereof. In some embodiments, the tricarbocyanine dye is indocyanine green.

DETAILED DESCRIPTION OF THE INVENTION

The only currently-available method for delineating tumor extent and margins during nephron-sparing surgery and in evaluating the presence of synchronous multifocality intra operatively is intra operative ultrasound. This technique requires the presence of an experienced ultrasonagraphy technician, which raises the cost and increases the difficulties in scheduling the surgery.

The present invention provides a new solution for delineating tumor extent and margins, as well as for evaluating the presence of multifocal tumors in renal cortical surgery. In the methods of the present invention, a non-toxic, fluorescent dye is administered to the patient immediately before or during the surgery. Although such dyes have been used as neuronal tracers and have been used by neurologists, they have not been widely used by practitioners to image other anatomical features or non-neural organ structures or tumors in animals or humans.

The present invention stems in part from studies we took in using the near infrared fluorescent dye indocyanine green ("ICG") to image cavernous nerves of the penis. When abdominal incisions were made, we noted that the kidneys were fluorescent for hours to days after ICG administration, even though ICG is cleared quickly from the circulation. Because we are urologists, we are aware that kidney tumors tend to be hypervascular and develop rich vascular beds that are not uniform. We formed the hypothesis that the vascular beds would tend to impede the flow of ICG out of the tumor. We realized that any difference in admission or retention of fluorescent dye between normal and tumor tissue would result in different amounts of fluorescence, and that these differences could be exploited to detect the presence or absence of tumors in areas of the kidney. We hypothesized that kidney tumors would tend to retain ICG more than areas of the kidney with normal vasculature, and that areas within the kidney that fluoresced when exposed to light of an appropriate excitation frequency would identify the presence of tumors.

In human clinical studies using ICG and near infrared (NIR) illumination, we found that, while normal kidney tissue fluoresced brightly upon administration of ICG and would gradually lose fluorescence over time, tumors flushed the dye quickly and were easily identified as non-fluorescing "black" or hypofluorescent "gray" areas against the "white" fluorescence of normal kidney parenchyma tissue.

Further, we found the invention permitted us to distinguish benign cysts, which do not have to be removed, from complex cysts with malignant elements. Benign cysts appeared even more fluorescent than did normal tissue. Without wishing to be bound by theory, it appears that fluid in benign cyst acts as a lens to focus the fluorescence of the dye. Complex cysts containing malignant elements, on the other hand, appeared hypo- or non-fluorescent under NIR illumination, like tumors. The most widely used categorization system for renal cysts is that developed by Bosniak, which classifies renal cysts according to the presence or absence of septa, calcification, wall thickening, and the presence of contrast enhancing tissue inside the complexes. The Bosniak system is well known and is reviewed in, for example, Warren and McFarlane, BJU J 95:939-942 (2005). Cysts that are categorized pre-surgically as category I or II upon MRI or CAT scanning are not generally removed. Sixty percent of category III cysts, however, have malignant elements, while the remaining 40% do not. Almost all category IV cysts contain malignant cells; thus, category IV cysts are removed by surgeons wherever possible. Further, some difficulties have arisen in differentiating category II from category III cysts. The invention permits the practitioner to quickly determine, even laparascopically, whether a renal cyst contains malignant elements and in particular whether a category III cyst is benign or contains malignant characteristics. The ability to readily distinguish benign cysts and those with malignant elements is another advantage provided by the invention.

The ability to visualize the tumors as "gray" or "black" areas in the midst of the normal kidney tissue, which shows as white under fluorescent illumination, provides at least three advantages. First, one goal during cancer surgery is to excise any tumor present without excising more area around the tumor than is necessary to ensure that no tumor tissue remains behind (this is known as leaving a "clear" or "negative" margin). The invention provides the ability to distinguish tumor tissue from normal kidney tissue visually in real time, facilitating the surgeon's ability to ensure that there is a negative margin. Second, and as a corollary, the ability to distinguish tumor from normal tissue means that the surgeon can spare as much normal kidney parenchyma as possible, thus impairing the patient's kidney function as little as possible given the extent of the patient's disease at the time of surgery. Third, the surgeon can see additional tumors that were not visible by preoperative imaging techniques, including CAT scans and magnetic resonance imaging. The ability to image the tumors essentially instantaneously and continuously during the operation is expected to significantly improve the surgeon's ability to spare normal tissue over conventional techniques while improving the removal of cancerous tissue.

A further advantage of the invention is the ability to determine whether the surgery has resulted in excision of all of the tumor in an area. For this purpose, the excised tumors and surrounding tissue are placed under the camera or other imaging device and examined during the operation. If the surgeon has succeeded in removing all the tumor, there will be a black, non-fluorescent area on the excision line surrounded by fluorescing normal tissue, whereas a lack of fluorescence on the excision line indicates that the surgeon has not provided a negative margin. This information can provide an indication in advance of a pathologist's report whether or not negative margins have been achieved, and may well replace the need for frozen sections and a pathologist's review to determine whether clear margins have been obtained. Thus, the present invention also relates to a method for visualizing a tumor margin in excised tissue. The presence of fluorescence on the excision line, indicates the presence of a tumor margin in the excised tissue.

If the number and size of the tumors is sufficiently small and, in the case of multi-focal tumors, if the distribution of the tumors is such that they can be removed while leaving a sufficient portion of the kidney to be functional, than the surgeon will be able to excise the tumor or tumors during partial nephrectomy/ies. If not, then the surgeon can perform a radical nephrectomy with the knowledge that he or she has done so because it was necessary. Determining whether the size and location of tumors requires a partial or radical nephrectomy is within the training and experience of the urologic surgeons who are ordinarily the persons performing the surgery.

In the methods of the invention, the fluorescent dye can be administered by any convenient route. Preferably, the dye is administered intravenously immediately before the nephron-sparing surgery or, even more preferably, during the operation. Most preferably, the dye is administered during the operation about 5 to 10 minutes before the surgeon expects to commence excision of the tumors. Conveniently, the dye is administered during the operation after the perirenal fat (the fat around the kidney) has been separated from the kidney. IV-administered fluorescent dye permits the dye to circulate through the patient's systemic circulation and rapidly appears in the kidney. After intravenous injection, ICG is bound within 1 to 2 seconds, mainly to globulins (1-lipoproteins), and remains intravascular, with normal vascular permeability. ICG is not metabolized in the body and is excreted exclusively by the liver, with a plasma half-life of 3 to 4 minutes. Thus, ICG is available in the vasculature almost immediately after injection.

Persons of skill will appreciate that the function of the kidney is as a specialized blood "filter." The organ has a large vascular surface area to facilitate separation and elimination of solutes. The pattern of circulation is one of "counter-current distribution" to maximize the difference of the concentration of solutes between the blood and urine. The tumors and the normal kidney tissue constitute two "compartments" with differences in the rate of dye uptake and of dye release, enhancing the ability to visualize and differentiate the tumors from normal renal tissue.

Fluorescent dyes typically have a known excitation frequency and a known emitting frequency. A light source emitting light of the dye's excitation frequency is positioned in proximity to the kidney so as to permit light from the light source to illuminate the kidney, or surrounding area, or both, in sufficient amount to excite the dye. A camera or other device capable of capturing an image of light received at the emission frequency of the dye is positioned to receive light emitted from dye in the kidney or surrounding area. Conveniently, the light goes through a filter capable of selectively passing light in the dye's emission frequency while blocking light at the dye's excitation frequency, thus permitting the receiving device to provide an image based on emission light from the dye. The normal kidney tissue, particularly the parenchyma, will quickly turn white under fluorescent illumination, while the tumors are either hypo- or non-fluorescent and are highly visible as black or gray areas.

Instrumentation

Conveniently, the device used for visualization of the kidney comprises both a laser and a camera. For convenience of reference, the discussion below refers to the exemplar dye ICG. Persons of skill will recognize that the other dyes mentioned herein as suitable for use in the inventive methods and procedures could be substituted for ICG, with the light source selected or adjusted to provide illumination optimized for the excitation frequency suitable for the particular dye chosen and the device for capturing the light emitted by the dye being selected or adjusted to be able to receive light of the appropriate frequency. For use with ICG, the laser conveniently consists of a laser diode providing a maximum of 3 W output at 806 nm. For other dyes, the laser diode is selected to provide a light with a wavelength at an excitation frequency appropriate for the dye selected.

The laser output is decollimated (i.e. optics are used to spread out the laser light from a tight beam) to provide even illumination over a field of view, for example, 7.6 cm by 7.6 cm at a working distance of 30 cm. The imaging system typically has a camera containing a charge-coupled device ("CCD") or a complementary symmetry metal oxide semiconductor ("CMOS") image sensor sensitive into the near infrared spectrum and, for use with ICG, is equipped with an 815 nm edge filter. In some embodiments, the laser or camera or both, are supported by an articulated arm connected to a wheeled base. This allows the imaging head to be moved into close proximity to the surgical table and for vertical movement of the head to attain an appropriate focal distance above the area of interest. The imaging head and extension arm that protrudes over the surgical field are typically covered with an optically transparent sterile drape. The laser can conveniently be activated by means of a computer command or by foot pedal. Laser/camera devices suitable for intra-operative imaging are commercially available. In some preferred embodiments, the laser/camera device is a SPY® Intra-operative Imaging System, a HELIOS® Imaging System, or a LUNA® Imaging System (all by Novadaq Technologies, Inc., Mississauga, Ontario, Canada).

In some embodiments, an instrument having an optical configuration similar to a fluorescence microscope may be used, in which a dichroic mirror is used to split the paths of the illumination (the excitation light). The excitation light reflects off the surface of the dichroic mirror into the objective, while the fluorescence emission passes through the dichroic mirror to the eyepiece or is converted into a signal to be presented on a screen. The instrument may further have an excitation filter or an emission filter, or both, to select the wavelengths appropriate for each function. Conveniently, the filters are interference filters, which block transmission of frequencies out of their bandpass.

For immediate observation, ICG is administered intravenously and as the dye passes through the vessels, the 806 nm light causes the dye to fluoresce, emitting light at 830 nm. For visualizing lymph nodes in the area of interest, the ICG is administered, allowed to accumulate at the area of interest and then is exposed to light at 806 nm. The emitted light is then captured using the imaging system. As noted, the capture system is typically a video camera containing a CCD or CMOS image sensor. The capture system feeds the image to a monitor so that the surgeon can visualize the fluorescence of the dye in the kidney in the area of interest in real time. Filters limit the light detected to a range appropriate for the selected fluorescence wavelengths. Optionally, the camera is also attached to a computer and the image is saved, which not only permits documentation of the extent to which the tumor or tumors extends, but also can be used for training urologic surgeons, nurses, and other medical staff. Typically, the time required for positioning the device is 2 minutes, while the total time that the vessels are illuminated with laser light is 30 seconds. It is contemplated that the surgeon will want to visualize different sections of the kidney as the operation progresses. If repositioning of the camera is required for some or all of the additional images, the duration of the operation may be modestly extended. It is anticipated that the benefit to the patient from better visualization of tumors will outweigh the cost to the patient in terms of extended operative time.

The methods described herein are suitable for use in mammals. Examples of suitable mammals include, but are not limited to, humans, non-human primates, dogs, cats, sheep, cows, pigs, horses, mice, rats, rabbits, and guinea pigs. Use in humans is primates, and particularly in humans, is preferred.

Dyes for Visualizing Tumors

As persons of skill are aware, fluorescent dyes have a particular excitation wavelength which causes the dye to fluoresce and emit light of a particular emission wavelength. Persons of skill will appreciate that a considerable literature is available in the art on the characteristics of different dyes, including their excitation wavelength and emission wavelength. This literature is well known, and will not be set forth in detail herein.

The dye is imaged by exciting it with a light that has an excitation wavelength appropriate for the particular dye used. Persons of skill are aware that a variety of dyes exist, and that each dye has an excitation wavelength and an emission wavelength. Some dyes, for example, fluoresce under ultraviolet ("UC") illumination while others fluoresce under incandescent illumination. The literature on the use of fluorescent dyes and probes in biological assays includes, for example, Dewey, T. G., Ed., Biophysical and Biochemical Aspects of Fluorescence Spectroscopy, Plenum Publishing (1991), Guilbault, G. G., Ed., Practical Fluorescence, Second Edition, Marcel Dekker (1990), Lakowicz, J. R., Ed., Topics in Fluorescence Spectroscopy: Techniques (Volume 1, 1991); Principles (Volume 2, 1991); Biochemical Applications (Volume 3, 1992); Probe Design and Chemical Sensing (Volume 4, 1994); Nonlinear and Two-Photon Induced Fluorescence (Volume 5, 1997); Protein Fluorescence (Volume 6, 2000); DNA Technology (Volume 7, 2003); Plenum Publishing, and Lakowicz, J. R., Principles of Fluorescence Spectroscopy, Second Edition, Plenum Publishing (1999) and W. T. Mason, ed., Fluorescent and Luminescent Probes for Biological Activity. A Practical Guide to Technology for Quantitative Real-Time Analysis, Academic Press (Second Ed., 1999).

Preferred fluorescent dyes suitable for use in the methods of the invention are non-toxic dyes which fluoresce when exposed to radiant energy, e.g. light. Preferably, the dyes are near infrared fluorochromes, or "NIRF" that emit light in the near infra red spectrum. In some embodiments, the dye is a tricarbocyanine dye, and in particularly preferred embodiments, is ICG. ICG is commercially available from, for example, Akorn, Inc. (Buffalo Grove, Ill.), which sells it under the name IC-GREEN™. In other embodiments the dye is selected from fluorescein isothiocyanate, rhodamine, phycoerythrin, phycocyanin, allophycocyanin, o-phthaldehyde, fluorescamine, Rose Bengal, trypan blue, and fluoro-gold. The dyes may be mixed or combined. In some embodiments, dye analogs may be used. A "dye analog" is a dye that has been chemically modified, but still retains its ability to fluoresce when exposed to radiant energy of an appropriate wavelength. ICG, Fast Blue and Fluorogold have all been used in mammals with low evidence of neuronal toxicity and are preferred.

Preferably, the dye selected is one that has low toxicity and has excitation and emission peaks within the "optical window" of tissue, where absorption due to endogenous chromophores is low. Near infrared light can therefore penetrate tissue to a depth of several millimeters to a few centimeters. ICG is particularly preferred both because it has low toxicity and because it has been approved by the Food and Drug Administration for several diagnostic purposes in humans. Further, its absorption (excitation) and emission peaks (805 and 835 nm, respectively) lie within the "optical window" of tissue. After intravenous injection, ICG is bound within 1 to 2 seconds, mainly to globulins (1-lipoproteins), and remains intravascular, with normal vascular permeability. ICG is not metabolized in the body and is excreted exclusively by the liver, with a plasma half-life of 3 to 4 minutes. It is not reabsorbed from the intestine and does not undergo enterohepatic recirculation. The recommended dose for ICG video angiography is 0.2 to 0.5 mg/kg; the maximum daily dose should not exceed 5 mg/kg.

For visualizing the kidney intraoperatively, the surgical field, or the portion of the surgical field in which imaging is desired, is illuminated with a light of the excitation wavelength or wavelengths suitable for the dye or dyes used. Ambient light may need to be dimmed to permit the fluorescence to be seen, and observation will typically require magnification. Where the excitation wavelength is outside of the visible range (where, for example, the excitation wavelength is in the ultraviolet or near infrared range), the light source may be designed to permit switching or "toggling" between the excitation wavelength and visible light. This permits the practitioner to note the position of the tissue of interest using the fluorescent property in relation to the rest of the surgical field and surrounding (but non-fluorescent) structures.

Typically, the dye is administered sufficiently before the intended surgery to permit the kidney to take up the dye, but not so long before the surgery that the dye has been cleared by the liver or otherwise eliminated from the body. Our initial animal studies with ICG involved injections of ICG into the penis to visualize nerves. Surprisingly, we found that the dye was taken up by the kidneys and caused intense fluorescence in the kidney 18 hours after injection. Thus, it appears that ICG can be used to image the kidney for at least a day after introduction into the patient, providing the practitioner with a considerable window in which to administer the dye.

As noted above, ICG circulates quickly when administered by IV, and binds the vasculature quickly. To increase the contrast against the tumors, which flush the dye more quickly than normal kidney tissue does, the dye is preferably administered immediately before (e.g., 0 to 1 hour) the operation commences or more preferably is administered during the operation.

The dye may also be administered locally to the kidney, for example, by injection into the renal artery. If the practitioner anticipates needing to visualize only a particular portion of the kidney, the dye may be administered locally into an artery providing blood to the desired portion of the kidney. This may be desirable if, for example, it is anticipated that the fluorescence of the entirety of the kidney would make it more difficult to see the portion of surgical interest. The anatomy of the kidney and of the arteries serving particular portions of the kidney are well known and need not be recounted in detail here. The particular arteries serving portions of the kidney are designated the superior segmental artery, the anterior superior segmental artery, the anterior inferior segmental artery, the inferior segmental artery, arcuate arteries, and interlobular arteries.

The maximum daily dosage of ICG for adults is 2 mg/kg. There is no data available describing the signs, symptoms, or laboratory findings accompanying an overdose of ICG. The $LD_{50}$ after IV administration ranges between 60 and 80 mg/kg in mice, 50 and 70 mg/kg in rats, and 50 to 80 mg/kg in rabbits.

EXAMPLES

Example 1

Intraoperative video angiography is performed with a laser-fluorescence imaging device (Novadaq Technologies, Inc., Mississauga, Ontario, Canada) consisting of a near infrared (NIR) laser light source and a NIR-sensitive digital camcorder. For measurements, the unit is positioned 30 to 40 cm from the area of interest. ICG, dissolved in water, is then injected as a bolus. When ICG is used as the imaging dye, NIR light emitted by the laser light source induces ICG fluorescence. The fluorescence is typically imaged by a video camera, with optical filtering to block ambient and laser light so that only ICG fluorescence is captured. Images can be viewed by the surgical team on screen in real time (typically 25 images/sec). Optionally, the images can be stored on the video camera or transferred to a computer or to storage media for later review or training of others.

Example 2

For studies of the use of methods of the invention in intraoperative imaging, the patients will typically meet the following inclusion criteria: a CT or MRI pre operative assessment of renal cortical tumor, pathology review and confirmation of renal cortical tumor, subjects for radical nephrectomy are stage T1-T4a, while subjects for partial nephrectomy are stage T1-T2, and subject is scheduled for partial or radical nephrectomy surgery. Typical exclusion criteria for the studies are: subject has significant liver disease, cirrhosis or liver insufficiency with abnormal liver function tests, as total bilirubin >1.5× normal and/or SGOT>2× normal, subject has uremia, serum creatinine >2.5 mg/dl, subject has a previous history of adverse reaction or allergy to ICG, iodine, shellfish or iodine dyes, subjects in whom the use of x-ray dye or ICG is contraindicated including development of adverse events when previously or presently administered, subject is a pregnant or lactating female, subject is participating in another drug, biologic and/or device protocol.

Patients will generally be retained in the studies wherever possible, but will be withdrawn if progressive impairment of liver and/or kidney function is diagnosed or if a subject develops unacceptable toxicity.

Example 3

Eligible subjects receive an intravenous infusion of ICG immediately prior to surgery. This infusion is administered over a 5 minute period, 1 mg/kg as a 2.5 mg/ml solution. Subjects with normal renal and liver function tests after ICG administration proceed with surgery. Abnormal renal and liver function levels are identified by the exclusion criteria noted in the previous Example. Subjects with abnormal results have their surgery but are not imaged. If, during surgery, insufficient fluorescence can be detected, additional infusions of ICG are administered intravenously and/or directly into the renal vessels and/or kidney.

Example 4

Following Institutional Review Board approval, a clinical trial of the invention was conducted. Ten patients presenting for radical or partial nephrectomy were enrolled in the trial. After the kidney was mobilized (typically, only one of the patient's kidneys is involved in such operations), ~10 cc (2.5 mg/ml) of ICG was injected intravenously. Shortly after injection, near infrared fluorescence (NIRF) imaging was conducted and recorded using a LUNA™ NIRF system (Novadaq Technologies Inc, Mississauga, Canada).

The first two patients selected presented for radical nephrectomy. In a radical nephrectomy, the perinephric fat is not dissected away from the kidney prior to the kidney being removed from the patient. We found that the perinephric fat was sufficiently thick that it impeded visualization of tumors while the kidney was still in the patient. After removal, the kidneys were studied by NIRF imaging to confirm that normal and tumor tissue could be distinguished. We found that the tumors and other lesions were clearly visible as hypo- or non-fluorescent areas, while the normal tissue was brightly fluorescent. Since the procedure did not provide an advantage for radical nephrectomy patients, however, all further patients in the study were patients presenting for partial nephrectomy. Eight of these patients were studied.

A total of 14 lesions, 9 solid and 5 cystic, were found in the ten patients. All of the tumors—8 clear cell, 2 papillary renal cell, and 1 chromophobe—were seen as hypo-fluorescent or non-fluorescent areas, clearly demarcated from the surrounding normal kidney parenchyma. Tumor size averaged 3.6 cm (1.5-6.5). In a partial nephrectomy, the perinephric fat around the kidney of interest is routinely removed or repositioned to allow access to the kidney. Thus, unlike for radical nephrectomy patients, the fat did not interfere with imaging. Both tumor and non-tumorous lesions were clearly visible under NIRF. Benign cysts were characterized by an increased fluorescence compared to the normal parenchyma, which we believe is due to the entrapped fluid acting as a lens to focus the near infrared light. Simple, thick walled cysts had similar characteristics to normal parenchyma. A hemorrhagic cyst found had NIRF characteristics of renal cell carcinoma. Since complex cysts such as this hemorrhagic cyst are often cancerous, it is useful to distinguish simple cysts (which are not generally removed) from complex cysts, (which would generally be removed). It is a further advantage of NIRF illumination that it permitted distinguishing between simple and complex cysts.

No hypersensitivity reactions or effects of the dye on postoperative hepatorenal function were observed. Microscopy and histological studies were performed on excised tissue. Upon microscopic examination, fluorescence was noted mainly in the tubules, proximal and distal, and minimally inside the glomeruli. Histological examination using hematoxylin and eosin staining confirmed the location of differential ICG fluorescence in tumor and normal renal tissue. All surgical margins were negative: 4 mm (the range of the margin was from 2-10 mm).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting the presence or absence of a tumor in an area of a kidney in a subject during a surgical operation, comprising:
   a) intravenously administering to said subject indocyanine green (ICG) which fluoresces at a near infrared emission wavelength when said dye is contacted with a near infrared excitation wavelength;
   b) illuminating said kidney during said operation with said near infrared excitation wavelength such that the ICG in said kidney fluoresces; and,
   c) detecting the presence or absence of fluorescence of the ICG in said kidney during said operation, using a video camera with optical filtering to block ambient and laser light, wherein detecting absence of fluorescence in said area indicates the presence of a tumor in said area, and detecting the presence of fluorescence in said area indicates the absence of a tumor in said area.

2. A method of claim 1, wherein there are a plurality of tumors in said kidney.

3. A method of claim 1, wherein said dye is administered locally into the renal artery, the superior segmental artery, anterior superior segmental artery, anterior inferior segmental artery, inferior segmental artery, an arcuate artery, or an interlobular artery.

4. A method of claim 1, wherein said tumor is visualized on an image display.

5. A method of claim 1, wherein said exposing of said kidney to said illumination comprising said excitation wavelength is by a laproscopic instrument.

6. A method of claim 1, wherein the subject is a human.

7. A method of claim 1, wherein said dye is administered during said surgical operation.

8. A method of claim 1, wherein said dye is administered within 1 hour before said surgical operation.

9. A method of claim 8, wherein said dye is administered within about ½ hour before said surgical operation.

10. A method of claim 8, wherein said dye is administered within about ½ hour before said surgical operation.

11. A method of visualizing a tumor in a kidney in a subject during a surgical operation, comprising:
   a) intravenously administering to said subject indocyanine green (ICG) which fluoresces at a near infrared emission wavelength when said dye is contacted with a near infrared excitation wavelength;
   b) illuminating said kidney during said operation with said near infrared excitation wavelength such that the ICG in said kidney fluoresces; and,
   c) visualizing the presence or absence of fluorescence of the ICG in said kidney during said operation, using a video camera with optical filtering to block ambient and laser light, wherein visualizing an area of said kidney in which fluorescence is absent is a visualization of said tumor.

12. A method of claim 11, wherein there are a plurality of tumors in said kidney.

13. A method of claim 11, wherein said dye is administered locally into the renal artery, the superior segmental artery, anterior superior segmental artery, anterior inferior segmental artery, inferior segmental artery, an arcuate artery, or an interlobular artery.

14. A method of claim 11, wherein said tumor is visualized on an image display.

15. A method of claim 11, wherein said exposing of said kidney to said illumination comprising said excitation wavelength is by a laproscopic instrument.

16. A method of claim 11, wherein the subject is a human.

17. A method of claim 11, wherein said dye is administered during said surgical operation.

18. A method of claim 11, wherein said dye is administered within 1 hour before said surgical operation.

19. A method of visualizing a tumor margin in tissue excised from a kidney during a surgical operation, comprising:
   a) intravenously administering to said subject indocyanine green (ICG) which fluoresces at a near infrared emission wavelength when said dye is contacted with a near infrared excitation wavelength,
   b) excising some or all of a tumor and surrounding tissue from said kidney during said operation,
   c) illuminating said kidney during said operation with said near infrared excitation wavelength such that the ICG in said kidney fluoresces; and
   d) visualizing the presence or absence of fluorescence of the ICG, using a video camera with optical filtering to block ambient and laser light, wherein visualizing fluorescence around said some or all of said tumor indicates the presence of a tumor margin, and an absence of said fluorescence around some or all of said tumor indicates the absence of a tumor margin.

20. A method of claim 19, wherein there are a plurality of tumors in said kidney.

21. A method of claim 19, wherein said dye is administered locally into the renal artery, the superior segmental artery, anterior superior segmental artery, anterior inferior segmental artery, inferior segmental artery, an arcuate artery, or an interlobular artery.

22. A method of claim 19, wherein said tumor and any surrounding tissue is visualized on an image display.

23. A method of claim 19, wherein the subject is a human.

24. A method of determining during a surgical operation whether a cyst in a kidney in a subject is benign or contains malignant cells, comprising:
   a) intravenously administering to said subject a dye indocyanine green (ICG) which fluoresces at an a near infrared emission wavelength when said dye ICG is contacted with an a near infrared excitation wavelength;
   b) illuminating said cyst during said operation with said near infrared excitation wavelength under conditions such that the ICG in said cyst fluoresces; and,
   c) comparing the fluorescence of said dye the ICG in said cyst during said operation to the fluorescence of surrounding kidney tissue, using a video camera with optical filtering to block ambient and laser light, wherein bright fluorescence in said cyst compared to said surrounding kidney tissue indicates that the cyst is benign and low or no fluorescence in said cyst compared to said surrounding kidney tissue indicates that the cyst contains malignant cells.

25. A method of claim 24, wherein said dye is administered locally into the renal artery, the superior segmental artery, anterior superior segmental artery, anterior inferior segmental artery, inferior segmental artery, an arcuate artery, or an interlobular artery.

26. A method of claim 24, wherein said cyst is visualized on an image display.

27. A method of claim 24, wherein said exposing of said cyst to said illumination comprising said excitation wavelength is by a laproscopic instrument.

* * * * *